US00PP26955P2

(12) United States Plant Patent
Wood

(10) Patent No.: US PP26,955 P2
(45) Date of Patent: Jul. 19, 2016

(54) ***HYDRANGEA* PLANT NAMED 'SMHMNUFB1'**

(50) Latin Name: *Hydrangea macrophylla*
Varietal Denomination: SMHMNUFB1

(71) Applicant: Timothy D. Wood, Spring Lake, MI (US)

(72) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 14/544,629

(22) Filed: Jan. 23, 2015

(51) Int. Cl.
*A01H 5/02* (2006.01)

(52) U.S. Cl.
USPC ..... Plt./250

(58) Field of Classification Search
USPC ..... Plt./226, 250
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Hydrangea* plant named 'SMHMNUFB1', characterized by its compact, upright, outwardly spreading and mounding plant habit; strong and sturdy stems; remontant flowering habit; dark green-colored leaves; mophead-type inflorescences with dark pink-colored sterile flowers that can easily be "blued" with aluminum sulfate treatments; and good garden performance.

2 Drawing Sheets

Botanical designation: *Hydrangea macrophylla.*
Cultivar denomination: 'SMHMNUFB1'.

BACKGROUND OF THE INVENTION

The present invention relates to a new and distinct *Hydrangea* plant, botanically known as *Hydrangea macrophylla* and hereinafter referred to by the name 'SMHMNUFB1'.

The new *Hydrangea* plant is a product of a planned breeding program conducted by the Inventor in Grand Haven, Mich. The objective of the breeding program was to develop new compact and reblooming *Hydrangea* plants with strong stems and attractive inflorescences.

The new *Hydrangea* plant originated from an open-pollination in July, 2008 of *Hydrangea macrophylla* 'Robert', disclosed in U.S. Plant Pat. No. 20,020, as the female, or seed parent and an unknown selection of *Hydrangea macrophylla*, as the male, or pollen, parent. The new *Hydrangea* plant was discovered and selected by the Inventor as a single flowering plant from within the progeny of the stated open-pollination in a controlled environment in Grand Haven, Mich. in June, 2011.

Asexual reproduction of the new *Hydrangea* plant by softwood cuttings in a controlled environment in Grand Haven, Mich. since June, 2011 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMHMNUFB1'. These characteristics in combination distinguish 'SMHMNUFB1' as a new and distinct *Hydrangea* plant:

1. Compact, upright, outwardly spreading and mounding plant habit.
2. Strong and sturdy stems.
3. Remontant flowering habit.
4. Dark green-colored leaves.
5. Mophead-type inflorescences with dark pink-colored sterile flowers that can easily be "blued" with aluminum sulfate treatments.
6. Good garden performance.

Plants of the new *Hydrangea* differ from plants of the female parent, 'Robert', in the following characteristics:

1. Plants of the new *Hydrangea* have stronger stems than plants of 'Robert'.
2. Sterile flower sepals of plants of the new *Hydrangea* are richer and more intense in color than sterile flower sepals of plants of 'Robert'.
3. Plants of the new *Hydrangea* are more easily "blued" with aluminum sulfate than plants of 'Robert'.
4. Plants of the new *Hydrangea* have a stronger reblooming habit than plants of 'Robert'.

Plants of the new *Hydrangea* can be compared to plants of *Hydrangea macrophylla* 'Nikko Blue', not patented. In side-by-side comparisons, plants of the new *Hydrangea* differed primarily from plants of 'Nikko Blue' in the following characteristics:

1. Sterile flower sepals of plants of the new *Hydrangea* were richer and more intense in color than sterile flower sepals of plants of 'Nikko Blue'.
2. Plants of the new *Hydrangea* had a stronger reblooming habit than plants of 'Nikko Blue'.

Plants of the new *Hydrangea* can also be compared to plants of *Hydrangea macrophylla* 'Berner', disclosed in U.S.

Plant Pat. No. 22,329. In side-by-side comparisons, plants of the new *Hydrangea* differed primarily from plants of 'Berner' in the following characteristics:

1. Sterile flower sepals of plants of the new *Hydrangea* were smaller and richer and more intense in color than sterile flower sepals of plants of 'Berner'.
2. Plants of the new *Hydrangea* had a stronger reblooming habit than plants of 'Berner'.
3. Plants of the new *Hydrangea* were more easily "blued" with aluminum sulfate than plants of 'Berner'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a top perspective view of a typical flowering plant of 'SMHMNUFB1' grown in a container.

The photograph on the second sheet is a close-up view of a typical flowering plant of 'SMHMNUFB1' that has been treated with aluminum sulfate.

DETAILED BOTANICAL DESCRIPTION

Plants used for the aforementioned photographs and the following description were grown during the summer in three-gallon containers in a polypropylene-covered shadehouse in Grand Haven, Mich. and under cultural practices typical of commercial *Hydrangea* production. During the production of the plants, day temperatures ranged from 18° C. to 27° C. and night temperatures ranged from 5° C. to 10° C. Plants of the new *Hydrangea* were two years old when the photographs and description were taken. Plants were overwintered in a polyethylene-covered greenhouse. Some plants were treated with aluminum sulfate to "blue" the flowers. During the production of the plants, the soil pH ranged from 5.0 to 6.0. In the following description, color references are made to The Royal Horticultural Society Colour Chart, 1995 Edition, except where general terms of ordinary dictionary significance are used.

Botanical description: *Hydrangea macrophylla* 'SMHMNUFB1'.

Parentage:

*Female, or seed, parent.*—*Hydrangea macrophylla* 'Robert', disclosed in U.S. Plant Pat. No. 20,020.

*Male, or pollen, parent.*—Unknown selection of *Hydrangea macrophylla*, not patented.

Propagation:

*Type cutting.*—By softwood cuttings.

*Time to initiate roots, summer.*—About 18 days at temperatures about 27° C.

*Time to produce a rooted young plant, summer.*—About 60 days at temperatures about 27° C.

*Root description.*—Fine to thick; fibrous; white and brown in color.

*Rooting habit.*—Freely branching; dense.

Plant description:

*Plant form and growth habit.*—Perennial deciduous shrub; compact, upright, outwardly spreading and mounding plant habit; strong and sturdy lateral branches; freely branching habit with about five lateral branches developing per plant; vigorous growth habit.

*Plant height.*—About 46 cm.

*Plant diameter or area of spread.*—About 69 cm.

*Lateral branches.*—Length: About 26 cm to 33 cm. Diameter: About 7 mm. Internode length: About 5 cm to 6.5 cm. Texture: Smooth, glabrous. Strength: Strong, sturdy. Aspect: About 15° to 45° from vertical. Color: Close to 145B.

Leaf description:

*Arrangement.*—Opposite, simple.

*Length.*—About 10 cm to 16 cm.

*Width.*—About 6 cm to 10 cm.

*Shape.*—Ovate.

*Apex.*—Acute.

*Base.*—Cuneate.

*Margin.*—Serrate.

*Texture, upper and lower surfaces.*—Smooth, glabrous; leathery.

*Venation pattern.*—Pinnate.

*Color.*—Developing leaves, upper surface: Close to 139B. Developing leaves, lower surface: Close to 138B. Fully expanded leaves, upper surface: Close to 139A; venation, close to 144B. Fully expanded leaves, lower surface: Close to 138B; venation, close to 138B.

*Petioles.*—Length: About 2 cm. Diameter: About 3 mm. Texture, upper and lower surfaces: Smooth, glabrous. Color, upper and lower surfaces: Close to 144B.

Flower description:

*Flower type and habit.*—Single sterile and fertile flowers arranged on terminal mophead cymes that are roughly hemispherical in shape; flowers face upright to outwardly.

*Fragrance.*—None detected.

*Natural flowering season.*—Plants flower throughout the summer in Grand Haven, Mich.; flowering remontant; flowers not persistent.

*Quantity of flowers.*—Freely flowering habit; about 48 fertile flowers and about 123 sterile flowers developing per inflorescence.

*Inflorescence height.*—About 10 cm.

*Inflorescence diameter.*—About 18 cm.

*Flower diameter, fertile flowers.*—About 6 mm.

*Flower depth (height), fertile flowers.*—About 1 cm.

*Flower diameter, sterile flowers.*—About 4.5 cm.

*Flower depth (height), sterile flowers.*—About 2 cm.

*Flower buds, fertile and sterile flowers.*—Length: About 3 mm. Diameter: About 3 mm. Shape: Obovate. Color, plants not treated with aluminum sulfate: Close to 145B. Color, plants treated with aluminum sulfate: Close to 145B.

*Petals, fertile flowers.*—Quantity and arrangement: About five in a single whorl. Length: About 3 mm. Width: About 2 mm. Shape: Ovate. Apex: Acute. Base: Cuneate. Margin: Entire. Texture, upper and lower surfaces: Smooth, glabrous. Color, plants not treated with aluminum sulfate: When opening, upper and lower surfaces: Close to 145B. Fully opened, upper and lower surfaces: Close to 75C; color does not change with development. Color, plants treated with aluminum sulfate: When opening, upper and lower surfaces: Close to 145B. Fully opened, upper and lower surfaces: Close to 97C; color does not change with development.

*Petals, sterile flowers*.—Quantity and arrangement: About four in a single whorl. Length: About 2 mm. Width: About 1 mm. Shape: Ovate. Apex: Acute. Base: Truncate. Margin: Entire. Texture, upper and lower surfaces: Smooth, glabrous. Color, plants not treated with aluminum sulfate: When opening, upper and lower surfaces: Close to 69A. Fully opened, upper and lower surfaces: Close to 69A; color does not change with development. Color, plants treated with aluminum sulfate: When opening, upper and lower surfaces: Close to 97C. Fully opened, upper and lower surfaces: Close to 97C; color does not change with development.

*Sepals, sterile flowers only*.—Quantity and arrangement: About four in a single whorl. Length: About 2.5 cm. Width: About 2 cm. Shape: Obovate. Apex: Obtuse. Base: Cuneate. Margin: Entire. Texture, upper and lower surfaces: Smooth, glabrous. Color, plants not treated with aluminum sulfate: When opening, upper surface: Close to 145B; towards the margins, close to 63B. When opening, lower surface: Close to 75C. Fully opened, upper surface: Close to 63C; color does not change with development. Fully opened, lower surface: Close to 75C; color does not change with development. Color, plants treated with aluminum sulfate: When opening, upper surface: Close to 145B; towards the margins, close to between 92A and 97A. When opening, lower surface: Close to between 92A and 97A. Fully opened, upper and lower surfaces: Close to between 92A and 97A; color does not change with development.

*Pedicels, fertile flowers*.—Length: About 3 mm. Diameter: About 1 mm. Angle: About 45° from inflorescence axis. Strength: Strong, sturdy. Texture: Smooth, glabrous. Color, plants not treated with aluminum sulfate: Close to 75C. Color, plants treated with aluminum sulfate: Close to 97C.

*Pedicels, sterile flowers*.—Length: About 1.5 cm to 2 cm. Diameter: About 1 mm. Angle: About 45° from inflorescence axis. Strength: Strong, sturdy. Texture: Slightly pubescent. Color, plants not treated with aluminum sulfate: Close to 75C. Color, plants treated with aluminum sulfate: Close to 97C.

*Reproductive organs, fertile flowers*.—Stamens: Quantity per flower: About ten. Filament length: About 2 mm. Filament color: Close to 75C. Anther shape: Round. Anther length: About 1 mm. Anther color: Close to 195A. Pollen amount: Scarce. Pollen color: Close to 155B. Pistils: Pistil quantity per flower: One, three to four-lobed. Pistil length: About 1 mm. Stigma shape: Oblong. Stigma color: Close to 75C. Style length: About 1 mm. Style color: Close to 155B. Ovary color: Close to 155B and 145D.

*Reproductive organs, sterile flowers*.—Stamens: Quantity per flower: About five. Filament length: About 0.5 mm. Filament color: Close to 155C. Anther shape: Lobed. Anther length: About 0.25 mm. Anther color: Close to 145C. Pollen amount: None observed. Pistils: Pistil quantity per flower: One, lobed. Pistil length: About 0.75 mm. Stigma shape: Oblong. Stigma color: Close to 76B. Style length: About 0.65 mm. Ovary color: Close to 155C and 145C.

*Seeds, observed on fertile flowers only*.—Quantity per inflorescence: Numerous. Size: Less than 0.1 mm by less than 0.1 mm; dust-like. Color: Brown.

Garden performance: Plants of the new *Hydrangea* have been observed to have good garden performance and to tolerate wind, rain and temperatures ranging from about −30° C. to about 36° C.

Disease & pest resistance: Plants of the new *Hydrangea* have been observed to be resistant to Mildew. Plants of the new *Hydrangea* have not been observed to be resistant to pests and other pathogens common to *Hydrangea* plants.

It is claimed:

1. A new and distinct *Hydrangea* plant named 'SMHMNUFB1' as illustrated and described.

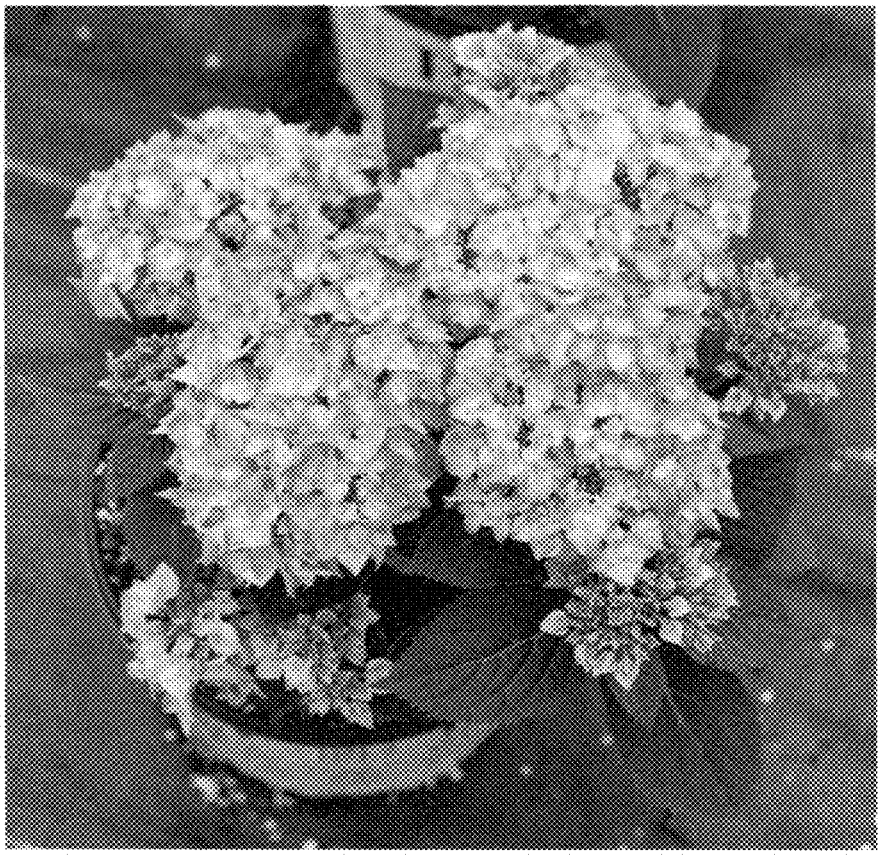

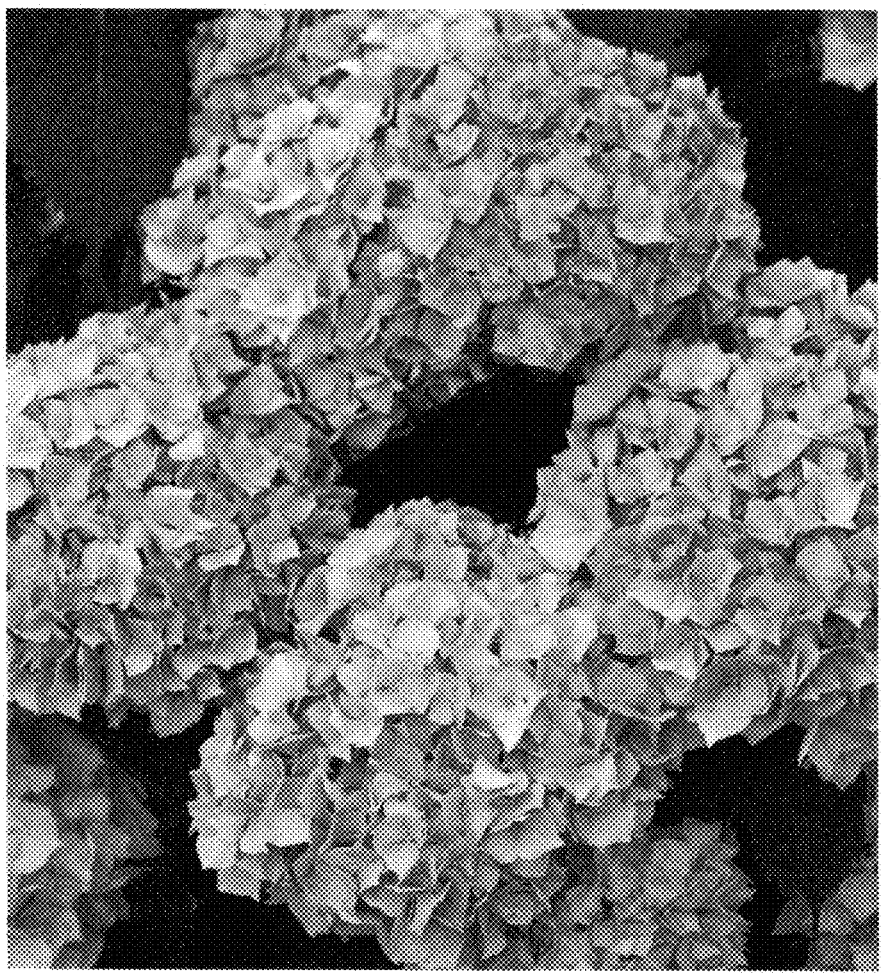

* * * * *